United States Patent [19]
Tapley et al.

[11] Patent Number: 5,914,101
[45] Date of Patent: Jun. 22, 1999

[54] ZINC OXIDE DISPERSIONS

[75] Inventors: Carole Allyson Maria Tapley, Stockton on Tees; Philip Laurence Lyth, Middlesbrough; Iain Michael Harper, Redcar, all of United Kingdom

[73] Assignee: Tioxide Specialties Limited, London, United Kingdom

[21] Appl. No.: 08/907,201

[22] Filed: Aug. 6, 1997

[30] Foreign Application Priority Data

Aug. 13, 1996 [GB] United Kingdom .................... 9616978

[51] Int. Cl.$^6$ .................. A61K 7/42; A61K 7/00
[52] U.S. Cl. ................ 424/59; 106/425; 106/426; 106/428; 106/436; 252/313.1; 423/99; 424/60; 424/400; 424/401
[58] Field of Search ................ 424/89, 60, 400, 424/401; 106/423, 436; 252/313.1; 423/436

[56] References Cited

U.S. PATENT DOCUMENTS

| | | |
|---|---|---|
| 2,885,366 | 5/1959 | Iler . |
| 3,472,840 | 10/1969 | Stone et al. ........................ 424/401 |
| 3,576,656 | 4/1971 | Webb et al. . |
| 4,923,518 | 5/1990 | Brand et al. . |
| 5,068,056 | 11/1991 | Robb . |
| 5,366,660 | 11/1994 | Tapley . |
| 5,516,457 | 5/1996 | Dahms . |
| 5,573,753 | 11/1996 | Tapley . |

FOREIGN PATENT DOCUMENTS

| | | |
|---|---|---|
| 0 595 471 | 5/1994 | European Pat. Off. . |
| 2-212414 | 8/1990 | Japan . |
| 3-183620 | 8/1991 | Japan . |
| 1 503 280 | 3/1978 | United Kingdom . |
| 2 184 356 | 6/1987 | United Kingdom . |
| 2 207 426 | 2/1989 | United Kingdom . |
| 2 207 434 | 2/1989 | United Kingdom . |
| 2 278 055 | 11/1994 | United Kingdom . |
| 90/06974 | 6/1990 | WIPO . |
| 92/13517 | 8/1992 | WIPO . |
| WO 93/22386 | 11/1993 | WIPO . |

OTHER PUBLICATIONS

Database WPI, Section Ch, Week 9522, Derwent Publications Ltd., London, GB; Class A60, AN 95–167072, XP002048129 & JP 07 089 710 A (Nippon Color Kogyo KK), Apr. 4, 21995.

*Primary Examiner*—Shelley A. Dodson

[57] ABSTRACT

A stabilised aqueous dispersion of particulate zinc oxide comprises water, a stabilising agent and zinc oxide, the particles of which are coated with dense amorphous silica. Useful stabilising agents include cellulose ethers which contain quaternary ammonium groups and polyalkylene glycols. The dispersions have excellent stability at high concentrations of zinc oxide and are useful for preparing sunscreen formulations, cosmetics and veterinary products.

28 Claims, No Drawings

ZINC OXIDE DISPERSIONS

This invention relates to dispersions of zinc oxide and particularly to aqueous dispersions of coated particles of zinc oxide.

Zinc oxide in a dispersed form is used in a number of formulations which contain water. Such formulations include sunscreening preparations, cosmetics and veterinary products. The preparation of these formulations is greatly eased if the zinc oxide is available in the form of an aqueous dispersion which can be readily incorporated into the formulation. However, stable dispersions of zinc oxide are difficult to prepare and the zinc oxide may dissolve at low or high pH values.

It is an object of this invention to provide a stable aqueous dispersion of zinc oxide which can be used to prepare such formulations.

According to the invention, a stabilised aqueous dispersion of particulate zinc oxide comprises water, a stabilising agent and zinc oxide, the particles of which are coated with dense amorphous silica which has been deposited on the surface of the zinc oxide particles by mixing an alkali metal silicate and an acid in the presence of zinc oxide particles in an aqueous suspension, the aqueous suspension being maintained at a pH of at least 8 during the mixing of said silicate and said acid.

The particle size of the zinc oxide is chosen to suit the final use for the dispersed particles. A particularly preferred stabilised dispersion according to the invention is useful in forming sunscreen preparations and, in this dispersion, the average primary particle size of the zinc oxide is in the range 0.005 to 0.20 micrometre. Preferably, the average primary particle size is in the range 0.01 to 0.10 micrometre and, more preferably, in the range 0.03 to 0.07 micrometre. The zinc oxide particles useful for sunscreen preparations preferably are substantially equiaxial and the average primary particle size is determined by measuring the average diameter of unagglomerated particles. According to this invention, the particles are provided with a coating. However, the preferred dimensions refer to the uncoated particles.

The stabilised dispersions of the invention are particularly useful when they contain a relatively high proportion of zinc oxide since this allows a user to have flexibility in producing the formulations in which the dispersions are used. Useful stabilised dispersions contain at least 40 per cent zinc oxide by weight and preferably the amount of zinc oxide is at least 50 per cent by weight. Particularly useful stabilised dispersions contain at least 60 per cent zinc oxide by weight. Normally, it is impractical to prepare a dispersion containing more than 75 per cent zinc oxide by weight.

Dense amorphous silica is a form of silica which is well known, particularly in the art of inorganic pigments, as a coating agent for particles. The dense silica is substantially non-porous and amorphous and generally forms a continuous coating over the particles of zinc oxide. It is characterised by the method by which it is formed, namely the dense silica is precipitated at alkaline suspension of zinc oxide having a pH of at least 8, and, preferably, a pH of from 9 to 11. In preparing the dispersions according to the invention precipitation takes place in the presence of zinc oxide particles. The dense silica is deposited by mixing an acid such as hydrochloric acid or sulphuric acid and an alkaline solution of an alkali metal silicate in the presence of zinc oxide to convert the silicate to dense amorphous silica. For instance, a solution of a soluble alkali metal silicate can be mixed with an alkaline suspension of the particles of zinc oxide to be coated and the resulting mixture is slowly acidified to deposit dense amorphous silica. Alternatively, there can be added to a suspension of the particles of zinc oxide an alkaline solution of an alkali metal silicate and, simultaneously, a mineral acid, to maintain the pH of the suspension at a value of at least 8, say 9 to 11, to form and deposit the required dense amorphous silica coating. Once the silica has been fully deposited, the pH of the suspension is normally adjusted by further addition of acid to a value in the range 6 to 8.

Generally the temperature of the suspension is maintained at a value of at least 60° C. and, possibly, up to 100° C., preferably from 70° C. to 90° C. during deposition of dense amorphous silica and the suspension will be stirred to maintain effective coating.

Any suitable alkali metal silicate can be used as the source of dense amorphous silica. Particularly useful are sodium and potassium silicates and preferably, also, the solution of the silicate is freshly prepared.

Normally, a dispersing agent is added to the zinc oxide suspension to ensure that the zinc oxide remains well distributed in the suspension during coating. A very convenient dispersing agent is an alkali metal silicate such as sodium or potassium silicate. This dispersing agent will usually become deposited as dense amorphous silica during the coating process. When added, the amount of silicate used as a dispersing agent is preferably in the range 1.0 to 5.0 weight per cent expressed as $SiO_2$ with respect to zinc oxide.

Sufficient dense amorphous silica is usually deposited upon the particles to form a complete layer over the individual particles. When the zinc oxide has an average primary particle size in the range 0.005 to 0.20 micrometre, the preferred amount of dense amorphous silica deposited is in the range 5 to 20 per cent by weight calculated as $SiO_2$ with respect to zinc oxide. Preferably, for this particle size, the amount of dense amorphous silica is in the range 7 to 12 per cent by weight as $SiO_2$ with respect to zinc oxide.

In addition to the coating of dense amorphous silica coatings of other hydrous oxides such as oxides of aluminium, zirconium or titanium may also be present on the zinc oxide particles. Although these deposited hydrous oxides are generally described as being present in the form of a coating, this does not necessarily imply that the zinc oxide particles are completely or uniformly covered with these hydrous oxides. The hydrous oxide can be deposited by any suitable means such as by hydrolysis of a soluble compound of the appropriate metal in the presence of a zinc oxide suspension.

Usually, after coating with dense amorphous silica and, if applicable, any other oxide, the zinc oxide particles are separated by filtration, for example, and dried.

In one embodiment of the invention, the stabilising agent used in the dispersion is a cellulose ether which contains quaternary ammonium groups. Particularly suitable stabilising agents are those polymers described in U.S. Pat. No. 3,472,840 which are polymers having a backbone of anhydroglucose units with pendant substituent groups containing quaternary ammonium functionality spaced along this backbone. Preferably, additional ether groups which do not contain a quaternary ammonium radical will also be present in the molecule. Such additional ether groups include alkyl, hydroxyalkyl, alkoxyalkyl and hydroxyalkoxyalkyl ether groups. The quaternary ammonium groups are preferably derived from a quaternary epoxide or a quaternary halohydrin. Particularly preferred stabilising agents are quaternary ammonium chlorides of hydroxyethyl cellulose reacted with a trimethyl ammonium substituted epoxide. Such products have been allocated the INCI Name Polyquaternium-10. Stabilising agents covered by this description and useful in this invention include those sold under the Trade Names UCARE Polymer JR-125, UCARE Polymer JR-400 and UCARE Polymer JR-30M.

The stabilising agents useful in this embodiment of the invention preferably have a weigth average molecular weight in the range 200,000 to 800,000.

The amount of cellulose ether stabilising agent used depends upon a number of factors including the particle size of the zinc oxide, the intended use of the dispersion and the concentration of zinc oxide in the dispersion. Preferably, the amount used is from 0.02 to 0.5 per cent by weight with respect to weight of zinc oxide. More preferably, the amount present is from 0.1 to 0.2 per cent by weight with respect to weight of zinc oxide. Usually the stabilising agent is added to the zinc oxide as described hereinafter after the zinc oxide has been coated with dense amorphous silica.

Usually, it is necessary to stir the cellulose ether stabilising agent with water to hydrate the polymer before it is mixed with the zinc oxide.

In a second embodiment of the invention, the stabilising agent used in the dispersion is a polyalkylene glycol. Suitable polyalkylene glycols include polyethylene glycols or polypropylene glycols but polyethylene glycol is preferred. Preferably, the polyethylene glycol which is used has a weight average molecular weight in the range 20,000 to 500,000.

The amount of polyalkylene glycol used can be varied according to the intended end use of the zinc oxide dispersion but normally the amount used is from 1.5 to 7.0 per cent by weight with respect to weight of zinc oxide. Preferably the amount is from 2.5 to 6.0 per cent by weight with respect to zinc oxide.

When polyethylene glycol is used to stabilise the emulsion it is normally necessary to hydrate solid polyethylene glycol by stirring with water and the resultant aqueous solution is usually then mixed with zinc oxide particles as described hereinafter.

The storage stability of the dispersions of the invention which utilise a cellulose ether containing quaternary ammonium groups as a stabilising agent can be improved by the addition of a thickener to the dispersion. Suitable thickeners include inorganic products such as swelling clays, for example Laponite (Trade Mark), and organic polymers such as polyalkylene glycols, especially polyethylene glycol and cellulose ether derivatives. Preferably, the polymeric thickeners have a weight average molecular weight greater than about 100,000.

The amount of thickener used is preferably in the range 1.5 to 7.0 per cent by weight with respect to weight of zinc oxide and more preferably in the range 2.5 to 6.0 per cent by weight with respect to zinc oxide.

Normally, the dispersion is prepared by intensive agitation of the coated zinc oxide particles with water. When the dispersion is intended for use in sunscreens it is particularly important that the zinc oxide is effectively dispersed as non-agglomerated particles. For this purpose a suitable means of agitation is to use a mill which employs a particulate grinding medium. Such mills are bead mills equipped with one or more agitators and using sand, glass beads, ceramic beads or other particles as the grinding medium. Particularly useful are those mills which operate at a high speed and depending on the size of mill a speed of the order of 2500 rev per minute (rpm) is not unusual. For instance mills operating at a speed of from 1000 rpm to 6000 rpm are suitable. Agitator mills in which the tip speed of the agitator is up to and can exceed 10 metres/sec are of use. If desired the mill can be cooled. After the agitation by milling has been carried out for the required time the dispersion is separated from the grinding medium by screening through a narrow gap. The stabilising agent and, when used, the thickener is preferably mixed with the zinc oxide before it is subjected to milling as this provides a more efficient mixing. However, either or both of the stabilising agent or the thickener can be mixed with the dispersion of coated zinc oxide after milling by any convenient means.

If desired conventional additives such as preservatives may also be added to the dispersion.

The dispersions according to the invention have shown excellent stability at high concentrations of zinc oxide and are very useful for preparing sunscreen formulations such as milks, lotions, and creams and cosmetics and veterinary products.

The invention is illustrated by the following examples.

EXAMPLE 1

An aqueous slurry of zinc oxide was prepared at a concentration of 250 g ZnO per litre by mixing demineralised water, nodular zinc oxide (average particle size 0.06 micrometre) and sodium silicate (equivalent to 2% $SiO_2$ by weight with respect to ZnO). The slurry was milled on a sand mill using Ottawa sand as a milling medium for 2 hours.

After separation of the sand the milled slurry was diluted to 170 g ZnO per litre with demineralised water and heated to 90° C. at which temperature it was maintained during subsequent deposition of dense amorphous silica. The pH of the slurry was adjusted to 9.4 with a solution containing 20% by weight hydrochloric acid and addition of a solution of sodium silicate (equivalent to 151 g $SiO_2$ per litre) was started. During the addition of sodium silicate 20% by weight hydrochloric acid was simultaneously added at a rate which maintained the pH of the slurry in the range 8.5 to 9.5. Addition was continued until the equivalent of 7.5% by weight $SiO_2$ with respect to ZnO had been added and the slurry was then stirred for 30 minutes at 90° C. Sufficient hydrochloric acid (20% HCl by weight) to reduce the pH of the slurry to 7.0 was then added over 30 minutes and the slurry was then stirred for a further 30 minutes.

The product was filtered and washed by repulping until the conductivity of the slurry was less than 150 $\mu S$. The zinc oxide coated with 9.5% by weight dense amorphous silica was spray dried (NIRO FD11) by feeding a slurry containing 250 g ZnO per litre with an inlet temperature of 500° C. and an outlet temperature of 100° C. and an atomiser disk speed of 18000 rpm.

0.225 g of a quaternised cationic hydroxyethyl cellulose sold under the Trade Name UCARE JR-125 (Union Carbide) was added to 99.775 g demineralised water and mixed with a propeller stirrer for 90 minutes to ensure complete hydration. 1.25 g of a preservative sold under the Trade Name Germaben II were added to this mixture followed by 150 g of zinc oxide coated as described above. The mixture was milled for 5 minutes in a high speed mill (Eiger M-50-VSE) using 60 g of 1 mm glass beads as a milling medium. 5.0 g of polyethylene glycol (Polyox WSR N-10) was added to the mixture and milling was continued for a further 15minutes. After separation of the glass beads, a dispersion of zinc oxide having a solids content of 58.5 per cent by weight was obtained.

A diluted dispersion was obtained by mixing 0.02 g of the above dispersion with 100 ml demineralised water and extinction coefficients were obtained at a wavelength of 308 nm ($E_{308}$), 360 nm ($E_{360}$) and 524 nm ($E_{524}$) using a UV/visible spectrometer (Perkin Elmer Lambda 2). The maximum extinction coefficient ($E_{max}$) and the wavelength of $E_{max}$ ($\lambda_{max}$) were also observed as follows.

| $E_{308}$ | $E_{360}$ | $E_{524}$ | $E_{max}$ | $\lambda_{max}$ |
|---|---|---|---|---|
| 13.7 | 14.5 | 3.3 | 17.3 | 373 |

After storage for 2 months no separation or sedimentation could be detected in the dispersion and the observed extinction coefficients were unchanged.

EXAMPLE 2

6.25 g of polyethylene glycol (Polyox WSR N- 10) was added to 100 g of demineralised water and mixed until fully hydrated. 150 g of zinc oxide coated with dense amorphous silica as described in Example 1 was added. The mixture was milled in a high speed bead mill (Eiger M-50-VSE) with 60 g of 1mm glass beads as the milling medium. The dispersion was milled for 20 minutes. The solids content of the dispersion after separation of the glass beads was 58.5% by weight.

0.02 g of the resultant dispersion was diluted with 100 ml demineralised water and extinction coefficients were measured as in Example 1. Results are given below.

| $E_{308}$ | $E_{360}$ | $E_{524}$ | $E_{max}$ | $\lambda_{max}$ |
|---|---|---|---|---|
| 14.1 | 14.9 | 3.3 | 17.5 | 373 |

After storage for 2 months no separation or sedimentation could be detected in the dispersion and the observed extinction coefficients were unchanged.

EXAMPLE 3

A dispersion of zinc oxide coated with dense amorphous silica was prepared as follows.

5 g of polyethylene glycol (Polyox WSR N- 10) was added to 94.625 g of demineralised water and mixed until fully hydrated. 0.375g of a preservative sold under the Trade Name Nipagin M Sodium (chemical name sodium methyl-4-hydroxybenzoate) were added to the mixture followed by 150 g of zinc oxide coated with dense amorphous silica as described in Example 1. The mixture was milled in a high speed bead mill (Eiger M-50-VSE) with 60 g of 1 mm glass beads as the milling medium. The dispersion was milled for 20 minutes. The solids content of the dispersion after separation of the glass beads was 58.7% by weight.

0.02 g of the resultant dispersion was diluted with 100 ml derineralised water and extinction coefficients were measured as in Example 1. Results are given below.

| $E_{308}$ | $E_{360}$ | $E_{524}$ | $E_{max}$ | $\lambda_{max}$ |
|---|---|---|---|---|
| 13.8 | 14.1 | 3.2 | 16.5 | 373 |

The sample was found to be stable for 2 months.

This dispersion was incorporated into a sunscreen lotion having the following formulation.

| | % by weight |
|---|---|
| Phase A | |
| 1) Light mineral oil | 6.5 |
| 2) Isopropyl myristate | 4.0 |
| 3) Grapeseed oil | 2.5 |
| 4) Stearyl alcohol | 1.0 |
| 5) White petroleumn jelly | 1.0 |
| Phase B | |
| 6) Demineralised water | 60.7 |
| 7) Xanthan gum (sold under the Trade Name Keltrol RD) | 0.2 |
| 8) D-Panthenol USP | 0.8 |
| 9) Glycerine BP | 4.0 |
| 10) Sorbitan stearate (sold under the Trade Name Span 60) | 6.0 |
| 11) Allantoin | 0.2 |
| 12) Disodium ricinoleamido MEA-sulfosuccinate (sold under the Trade Name Rewoderm S1333) | 0.2 |
| 13) Dispersion of zinc oxide (58.7% ZnO by weight) | 12.5 |
| Phase C | |
| 14) Mixture of alkyl parabens in phenoxyethanol (sold under the Trade Name Phenonip) | 0.4 |

Ingredient 7 was dispersed in water (ingredient 6) and ingredient 9 was added. Then ingredient 13 was added with vigorous stirring followed by the remaining ingredients of Phase B. This mixture was then heated to 80° C. with constant stirring. The ingredients of Phase A were mixed and heated to 80° C. Phase A was then added to Phase B at 80° C. and the two phases mixed with a rotor/stator mixer for 2 minutes at 80° C. The resultant mixture was cooled with stirring to 45° C. and Phase C was added. Stirring was continued until the product had cooled to 30° C.

The resultant lotion had an in-vitro Sun Protection Factor (SPF) of 6.6, when measured by the method of Diffey and Robson, J. Soc. Cosmet. Chem., 40, 127–133, (1989).

EXAMPLE 4

A further sample of the zinc oxide dispersion used in Example 3 was incorporated into a sunscreen lotion having the following formulation.

| | % by weight |
|---|---|
| Phase A | |
| 1) Emulsifier (Arlacel 165 from ICI Surfactants) | 5.0 |
| 2) Stearyl Alcohol | 1.0 |
| 3) Light mineral oil | 6.0 |
| 4) Sweet Almond oil | 3.0 |
| 5) Dimethicone fluid - 350 cs (sold under the Trade Name Dow Corning 200 Fluid) | 2.0 |
| 6) $C_{12-15}$ Alkyl Benzoate (sold under the Trade Name Finsolv TN) | 4.5 |
| Phase B | |
| 7) Demineralised water | 61.4 |
| 8) Carbopol Ultrez 10 Polymer (from B F Goodrich Co) | 0.2 |
| 9) Glycerine BP | 4.0 |
| 10) Dispersion of zinc oxide (58.7% ZnO by weight) | 12.5 |
| Phase C | |
| 11) Mixture of alkyl parabens in phenoxyethanol (Sold under the Trade Name Phenonip) | 0.4 |

Ingredient 8 was dispersed in the water (ingredient 7) and ingredient 9 was added followed by ingredient 10 with vigorous stirring. The ingredients of Phase A were mixed and Phases A and B were heated to 80° C. Phase A was added to Phase B whilst the mixture was stirred on a rotor/stator mixer. Mixing was continued until the mixture was fully homogenised. The lotion produced was cooled with moderate stirring and Phase C was added when the temperature reached 45° C. Stirring was continued until the temperature reached 30° C.

The lotion was tested using the method of Diffey and Robson and found to have an SPF of 6.5

EXAMPLE 5

A further sample of the zinc oxide dispersion used in Example 3 was incorporated into a sunscreen lotion having the following formulation.

| | % by weight |
|---|---|
| Phase A | |
| 1) Emulsifier (Arlacel 165 from ICI Surfactants) | 5.0 |
| 2) Stearyl alcohol | 1.0 |
| 3) Light mineral oil | 6.0 |
| 4) Sweet Almond oil | 3.0 |
| 5) Dimethicone fluid - 350 cs (sold under the Trade Name Dow Corning 200 Fluid) | 2.0 |
| 6) $C_{12-15}$ Alkyl Benzoate (sold under the Trade Name Finsolv TN) | 4.5 |
| Phase B | |
| 7) Demineralised water | 53.9 |
| 8) Xanthan gum (sold under the Trade Name Keltrol RD) | 0.2 |
| 9) Glycerine BP | 4.0 |
| 10) Dispersion of zinc oxide (58.7% ZnO by weight) | 20.0 |
| Phase C | |
| 11) Mixture of alkyl parabens in phenoxyethanol (sold under the Trade Name Phenonip) | 0.4 |

Ingredient 8 was dispersed in water (ingredient 7) and ingredient 9 was added. Then ingredient 10 was added with vigorous stirring. This mixture was then heated to 80° C. with constant stirring. The ingredients of Phase A were mixed and heated to 80° C. Phase A was then added to Phase B at 80° C. and the two phases mixed with a rotor/stator mixer for 3 minutes at 80° C. The resultant mixture was cooled with stirring to 45° C. and Phase C was added. Stirring was continued until the product had cooled to 30° C.

The resultant lotion, when tested by the Diffey and Robson method, had an SPF of 12.5.

EXAMPLE 6

A further sample of the dispersion of zinc oxide used in Example 3 was incorporated into a sunscreen lotion having the following formulation.

| | % by weight |
|---|---|
| Phase A | |
| 1) Light mineral oil | 4.0 |
| 2) Octyl palmitate | 6.0 |
| 3) Cetyl/stearyl alcohol | 1.0 |
| 4) Emulsifying mixture (Hydrolactol 70 from Gattefosse SA) | 16.0 |
| 5) Dimethicone fluid (sold under the Trade Name Dow Corning 593 Fluid) | 3.0 |
| Phase B | |
| 6) Demineralised water | 57.1 |
| 7) Dispersion of zinc oxide (58.7% ZnO by weight) | 12.5 |

-continued

| | % by weight |
|---|---|
| Phase C | |
| 8) Mixture of alkyl parabens in phenoxyethanol (sold under the Trade Name Phenonip) | 0.4 |

The ingredients of Phase A and Phase B were separately mixed and heated to 80° C. Phase A was added to Phase B and mixed using a rotor/stator mixer for 2 minutes. The lotion was cooled with stirring, Phase C was added at 45° C. and stirring was continued until the temperature reached 30° C.

The lotion had an SPF of 6.0 when tested by the Diffey and Robson method.

We claim:

1. A stabilised aqueous dispersion of particulate zinc oxide comprising water, a stabilising agent and zinc oxide, the particles of which are coated with dense amorphous silica which has been deposited on the surface of the zinc oxide particles by mixing an alkali metal silicate and an acid in the presence of zinc oxide particles in an aqueous suspension, the aqueous suspension being maintained at a pH of at least 8 during the mixing of said silicate and said acid.

2. A stabilised aqueous dispersion according to claim 1 in which the particles of uncoated zinc oxide have an average primary particle size in the range 0.005 to 0.20 micrometre.

3. A stabilised aqueous dispersion according to claim 1 which contains at least 40 per cent zinc oxide by weight.

4. A stabilised aqueous dispersion according to claim 1 which contains not more than 75 per cent zinc oxide by weight.

5. A stabilised aqueous dispersion according to claim 2 in which the zinc oxide particles are coated with dense amorphous silica in an amount between 5 and 20 per cent by weight calculated as $SiO_2$ with respect to zinc oxide.

6. A stabilised aqueous dispersion according to claim 1 in which the zinc oxide particles are coated with a hydrous oxide in addition to the coating of dense amorphous silica said hydrous oxide being a hydrous oxide of a metal selected from the group consisting of aluminium, zirconium and titanium.

7. A stabilised aqueous dispersion according to claim 1 in which the stabilising agent is a cellulose ether which contains quaternary ammonium groups.

8. A stabilised aqueous dispersion according to claim 7 in which the stabilising agent is a polymer having a backbone of anhydroglucose units with pendant substituent groups containing quaternary ammonium functionality spaced along the backbone.

9. A stabilised aqueous dispersion according to claim 8 in which ether groups which do not contain a quaternary ammonium radical are present in the polymer molecule.

10. A stabilised aqueous dispersion according to claim 7 in which the stabilising agent is the reaction product of a quaternary ammonium chloride of hydroxyethyl cellulose and a trimethyl ammonium substituted epoxide.

11. A stabilised aqueous dispersion according to claim 7 in which the stabilising agent has a weight average molecular weight in the range 200,000 to 800,000.

12. A stabilised aqueous dispersion according to claim 7 in which the stabilising agent is present in an amount in the range 0.02 to 0.5 per cent by weight with respect to weight of zinc oxide.

13. A stabilised aqueous dispersion according to claim 7 which contains a thickener selected from the group consisting of swelling clays, polyalkylene glycols and cellulose ether derivatives.

14. A stabilised aqueous dispersion according to claim 13 in which the thickener is a polymer having a molecular weight greater than 100,000.

15. A stabilised aqueous dispersion according to claim 13 in which the thickener is present in an amount in the range 1.5 to 7.0 per cent by weight with respect to weight of zinc oxide.

16. A stabilised aqueous dispersion according to claim 1 in which the stabilising agent is a polyalkylene glycol.

17. A stabilised aqueous dispersion according to claim 16 in which the stabilising agent is a polyethylene glycol having a weight average molecular weight in the range 20,000 to 500,000.

18. A stabilised aqueous dispersion according to claim 16 in which the polyalkylene glycol is present in an amount in the range 1.5 to 7.0 per cent by weight with respect to weight of zinc oxide.

19. A method for the preparation of a stabilised aqueous dispersion comprising mixing water, a stabilising agent and zinc oxide the particles of which are coated with dense amorphous silica which has been deposited on the zinc oxide particles by mixing an alkali metal silicate and an acid in the presence of zinc oxide particles in an aqueous suspension, the aqueous suspension being maintained at a pH of at least 8 during mixing of said silicate and said acid.

20. A method according to claim 19 in which the acid is selected from the group consisting of hydrochloric acid and sulphuric acid.

21. A method according to claim 19 in which a solution of an alkali metal silicate and an alkaline suspension of zinc oxide particles are mixed and the resulting mixture is slowly acidified.

22. A method according to claim 19 in which an alkaline solution of an alkali metal silicate and a mineral acid are simultaneously added to a suspension of zinc oxide particles, the suspension being maintained at a pH of at least 8 during addition of the silicate and the acid.

23. A method according to claim 19 in which the suspension of zinc oxide particles is maintained at a temperature in the range 60° C. to 100° C. during deposition of the dense amorphous silica.

24. A method according to claim 19 in which a dispersing agent selected from the group consisting of sodium silicate and potassium silicate is present in the zinc oxide dispersion during deposition of dense amorphous silica.

25. A method according to claim 24 in which the dispersing agent is present in an amount in the range 1.0 to 5.0 per cent by weight expressed as $SiO_2$ with respect to zinc oxide.

26. A method according to claim 19 in which the coated particles of zinc oxide are mixed with water in a bead mill which employs a grinding medium selected from the group consisting of sand, glass beads and ceramic beads.

27. A method according to claim 26 in which the mill is operated at a speed of 1000 rpm to 6000 rpm.

28. A method according to claim 26 in which the stabilising agent and, when used, a thickener are mixed with the zinc oxide before milling.

* * * * *